United States Patent
Branellec et al.

(10) Patent No.: US 6,410,011 B1
(45) Date of Patent: *Jun. 25, 2002

(54) GENE THERAPY FOR RESTENOSIS USING AN ADENOVIRAL VECTOR

(75) Inventors: Didier Branellec, La Varenne Saint-Hilaire; Jean-François Dedieu, Paris; Patrice Denefle, Saint Maur; Laurent Feldman, Paris; Michel Perricaudet, Ecrosnes; Philippe Gabriel Steg, Paris, all of (FR)

(73) Assignee: Aventis Pharma S.A., Antony (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/633,769

(22) PCT Filed: Aug. 10, 1995

(86) PCT No.: PCT/FR95/01074

§ 371 (c)(1),
(2), (4) Date: Jun. 20, 1996

(87) PCT Pub. No.: WO96/05321

PCT Pub. Date: Feb. 22, 1996

(30) Foreign Application Priority Data

Aug. 17, 1994 (FR) .............................. 94 10083

(51) Int. Cl.$^7$ ...................... A61K 48/00; C12N 15/861
(52) U.S. Cl. ..................... 424/93.2; 514/44; 435/320.1; 435/455; 435/456
(58) Field of Search .......................... 435/320.1, 240.2, 435/240.1, 172.1, 172.2, 456, 455; 424/93.21, 93.2; 514/2, 44

(56) References Cited

U.S. PATENT DOCUMENTS 5,328,470 A * 7/1994 Nabel et al. ................ 604/101
6,290,949 B1 * 9/2001 French et al. .............. 424/93.2

FOREIGN PATENT DOCUMENTS

WO    WO 97/06826    * 2/1997

OTHER PUBLICATIONS

Grable et al., "cis and trans requirements for selective packaging of adenovirus type 5 DNA", J. Virol. 66 (2): 723–731, Feb. 1992.*

LeClerc Et Al J. Clin. Invest. 90: 936, 1992, Sep. 15, 1997.*

La Font Et Al., Lancet, 346: 1442–1443, 1995.*

Marshall, Science, 269: 1050–1055, 1995.*

Nabel et al., Ann. New York Acad. Sci., 714: 247–252 1994.*

Ohno et al., Science, 265: 781–784, 1994.*

Steg Et Al., J. Amer. Coll. Card. Mar. 17, 1993 vol. 0 949–110.*

Steg Et Al., J. Amer. Coll. Card. Mar. 17, 1994 43rd Annual Scientific Session #3554.*

* cited by examiner

Primary Examiner—Scott D. Priebe
(74) Attorney, Agent, or Firm—Finnegan, Henderson, Farabow, Garrett & Dunner LLP (57) ABSTRACT

A method for treating restenosis by gene therapy is disclosed, said method comprising delivering a recombinant suicide-gene-containing adenovirus.

24 Claims, 4 Drawing Sheets

GENE THERAPY FOR RESTENOSIS USING AN ADENOVIRAL VECTOR

The present invention relates to a method for treatment of restenosis by gene therapy, comprising the administration of a recombinant adenovirus containing a suicide gene. It also relates to particular pharmaceutical compositions permitting the local and effective administration of recombinant viruses.

Atherosclerosis is a complex, polygenic disease which is defined in histological terms by deposits (lipid or fibrolipid plaques) of lipids and of other blood derivatives in the wall of the large arteries (aorta, coronary arteries, carotid). These plaques, which are more or less calcified according to the degree of progression of the process, may be coupled with lesions and are associated with the accumulation in the arteries of fatty deposits consisting essentially of cholesterol esters. These plaques are accompanied by a thickening of the arterial wall, with hypertrophy of the smooth muscle, appearance of foam cells and accumulation of fibrous tissue. The atheromatous plaque protrudes markedly from the wall, endowing it with a stenosing character responsible for vascular occlusions by atheroma, thrombosis or embolism, which occur in those patients who are most affected. These lesions can hence lead to very serious cardiovascular pathologies such as infarction, sudden death, cardiac insufficiency, stroke, and the like.

Since 1977, the technique of angioplasty has been developed to permit a non-surgical intervention in respect of the atherosclerosis plaque. However, the treatment of an atherosclerotic lesion by angioplasty results very frequently (up to 50% of cases in some studies) in a restenosis following mechanical injury of the arterial wall. A key event in this mechanism is the proliferation and migration of vascular smooth muscle cells (VSMC) from the media to the intima, in particular as a result of the absence of protection and/or feedback control exercised by the endothelial cells of the intima.

The treatment of restenosis by administration of chemical or proteinaceous substances capable of killing vascular smooth muscle cells has been proposed in the prior art. Thus, psolaren derivatives, incorporated by proliferative cells and then sensitizing these cells to the action of light, have been used (March et al., 1993, circulation, 87:184–191). Similarly, some cytotoxins consisting of a fusion protein between a plant or bacterial toxin fragment and a growth factor have also been used (Pickering et al., J. Clin. Invest., 1993, 91:724–729; Biro et al., 1992, Circ. Res., 71:640–645; Casscells et al., Proc. Natl. Acad. Sci. USA, 1992, 89:7159–7163). However, these treatments have many drawbacks, such as their low specificity, their indifferent efficacy, a considerable delay in acting and a potential toxicity.

The present invention offers an advantageous approach to this problem. The present invention provides, in effect, an especially effective and selective method for the treatment of postangioplasty restenosis by gene therapy. The method of the present invention consists mainly in administering a recombinant adenovirus containing a suicide gene, capable of specifically sensitizing proliferating vascular smooth muscle cells to a therapeutic agent. Simultaneous or subsequent administration of this therapeutic agent then brings about the selective death of the sensitized cells.

The advantages of the present invention lie, in particular, in the high capacity of the adenoviruses of the invention to infect proliferating vascular smooth muscle cells. This enables relatively small amounts of active principle (recombinant adenovirus) to be used, and also permits an effective and very rapid action on the sites to be treated. The adenoviruses of the invention are also capable of expressing at very high levels the suicide genes introduced, thereby endowing them with a very effective therapeutic action. Furthermore, on account of their episomal character, the adenoviruses of the invention have a limited persistence in proliferative cells, and hence a transient effect entirely suited to the desired therapeutic effect. Lastly, the Applicant has also developed an especially advantageous method of administration, which enables certain target cells essential to the desired therapeutic effect to be infected with great efficacy.

A first object of the invention hence relates to the use of a defective recombinant adenovirus containing a suicide gene for the preparation of a pharmaceutical composition intended for the treatment of restenosis.

As mentioned above, for the purposes of the present invention, suicide gene is understood to mean any gene whose expression product endows the infected cell with a sensitivity to a therapeutic agent. As an example, there may be mentioned the thymidine kinase gene, whose expression product endows mammalian cells with a sensitivity to certain therapeutic agents such as ganciclovir or acyclovir, or the cytosine deaminase gene, whose expression product endows mammalian cells with a sensitivity to 5-fluorocytosine (5-FC).

Herpes simplex virus thymidine kinase is capable of phosphorylating nucleoside analogues such as acyclovir and ganciclovir. These modified molecules may be incorporated in a DNA chain undergoing elongation, which results in the cessation of DNA synthesis and brings about the death of the cell (F. L. Moolten, Cancer Res. 46 (1986) 5276). This strategy thus enables cells expressing the TK gene to be specifically eliminated. Furthermore, since the DNA synthesis is the target of the toxicity, only cells undergoing division are affected.

More preferably, the human herpesvirus thymidine kinase (hHSV-1 TK) gene is used in the context of the present invention. The sequence of this gene has been described in the literature (see, in particular, McKnight et al., Nucleic Acid. Res. 8 (1980) 5931). It is also possible to use derivatives of this sequence displaying greater substrate specificity or better kinase activity. Such derivatives may, in particular, be obtained by mutagenesis at the binding site, as described previously (Balasubramaniam et al., J. Gen. Virol. 71 (1990) 2979; Munir et al., JBC 267 (1992) 6584).

It is also possible to use the cytosine deaminase gene, whose expression product endows mammalian cells with a sensitivity to 5-fluorocytosine (5-FC). Cytosine deaminase is capable of catalyzing the deamination of cytosine to uracil. Cells which express this gene are hence capable of converting 5-fluorocytosine (5-FC) to 5-fluorouracil (5-FU), which is a toxic metabolite. The sequence of this gene has been described in the literature (Anderson et al., Arch. Microbiol. 152 (1989) 115).

More generally, any gene capable of endowing infected cells with a sensitivity to a therapeutic agent may be used in the context of the present invention. The thymidine kinase gene constitutes an especially advantageous embodiment.

For the construction of the adenoviruses according to the invention, different serotypes may be used. There are, in effect, many serotypes of adenovirus, whose structure and properties vary somewhat. Among these serotypes, it is preferable however to use, in the context of the present invention, human adenoviruses type 2 or 5 (Ad 2 or Ad 5) or adenoviruses of animal origin (see Application FR 93/05954). Among adenoviruses of animal origin which are usable in the context of the present invention, adenoviruses of canine, bovine, murine (for example: Mav1, Beard et al., Virology 75 (1990) 81), ovine, porcine, avian or alternatively simian (for example: SAV) origin may be mentioned. Preferably, the adenovirus of animal origin is a canine adenovirus, more preferably a CAV2 adenovirus [Manhattan or A26/61 (ATCC VR-800) strain, for example]. It is preferable to use adenoviruses of human or canine or mixed origin in the context of the invention.

As stated above, the adenoviruses according to the invention are defective, that is to say they are incapable of replicating autonomously in the target cell. Generally, the genome of the defective adenoviruses used the context of the present invention hence lacks at least the sequences needed for replication of the said virus in the infected cell. These regions may be either removed (in their entirety or partially), or rendered non-functional, or replaced by other sequences, and in particular by the suicide gene. Preferably, the defective adenovirus nevertheless retains the sequences of its genome which are needed for encapsidation of the viral particles.

Preferably, the defective adenoviruses of the invention comprise the ITRs, a sequence permitting encapsidation and the suicide gene. Still more preferably, in the genome of the adenoviruses of the invention, the E1 gene and at least one of the genes E2, E4, L1–L5 are non-functional. The viral gene of interest may be rendered non-functional by any technique known to a person skilled in the art, and in particular by total elimination, substitution, partial deletion or addition of one or more bases in the gene or genes of interest. Such modifications may be obtained in vitro (on the isolated DNA) or in situ, for example by means of genetic engineering techniques, or alternatively by treatment using mutagenic agents.

More preferably, a defective adenovirus rendered nonfunctional by a total or partial deletion of the E1 region and a deletion in the E4 region is used. The E4 region comprises 7 reading frames. The deletion in the E4 region may be transcomplemented by the presence, in the cell line used for multiplication of the viruses, either simply of the reading frame ORF6, or of the reading frames ORF6 and ORF6/7.

Preferred adenoviruses according to the invention are chosen from the following:

Defective recombinant adenovirus ΔE1, ΔE4 comprising a deletion of all or part of the E1 region and a deletion of all or part of the E4 region.

Defective recombinant adenovirus ΔE1, ORF3⁻, ORF6⁻ comprising a deletion of all or part of the E1 region and of nucleotides 34801–34329 and 34115–33126 of the E4 region.

Defective recombinant adenovirus ΔE1, ΔE4, ORF1⁺ comprising a deletion of all or part of the E1 region and a deletion of the E4 region except for the reading frame ORF1. More specifically, the deletion in the E4 region has its 5' end included in the reading frame ORF7 and its 3' end included in the reading frame ORF2. For example, in the region covering nucleotides 33093–35053.

Defective recombinant adenovirus ΔE1, ΔE4, ORF4⁺ comprising a deletion of all or part of the E1 region and a deletion of the E4 region except for the reading frame ORF4. More especially, two deletions are carried out, one whose 5' end is included in the reading frame ORF7 and whose 3' end is located in the reading frame ORF6, the other whose 5' end is included in the reading frame ORF3 and whose 3' end is located in the reading frame ORF1 or in the promoter region of E4. For example, a deletion covering nucleotides 33093–33695 and a deletion covering nucleotides 34634–35355.

Defective recombinant adenovirus ΔE1, ΔE4 comprising a deletion of all or part of the E1 region and a deletion covering the whole of the E4 region, chosen, for example, from the following deletions: nucleotides 32720–35835, or 33466–35355, or 33093–35355.

The construction of these vectors is described in Patents No. FR 9500749 and No. FR 9506532.

The defective recombinant adenoviruses according to the invention may be prepared by any technique known to a person skilled in the art (Levrero et al., Gene 101 (1991) 195, EP 185,573; Graham, EMBO J. 3 (1984) 2917). In particular, they may be prepared by homologous recombination between an adenovirus and a plasmid carrying, inter alia, the suicide gene. Homologous recombination takes place after cotransfection of the said adenovirus and said plasmid into a suitable cell line. The cell line used should preferably (i) be transformable by the said elements, and (ii) contain the sequences capable of complementing the portion of the genome of the defective adenovirus, preferably in integrated form in order to avoid risks of recombination. As an example of a line, there may be mentioned the human embryonic kidney line 293 (Graham et al., J. Gen. Virol. 36 (1977) 59) which contains, in particular, integrated in its genome, the left-hand portion of the genome of an Ad5 adenovirus (12%). Strategies of construction of vectors derived from adenoviruses have also been described in Applications Nos. FR 93/05954 and FR 93/08596.

Thereafter, the adenoviruses which have multiplied are recovered and purified according to standard techniques of molecular biology, as illustrated in the examples.

Advantageously, in the adenoviruses of the invention, the suicide gene is placed under the control of a promoter permitting its expression in infected cells. This promoter can be the one belonging to the suicide gene, a heterologous promoter or a synthetic promoter. In particular, promoters originating from eukaryotic or viral genes may be used. For example, it is possible to use promoter sequences originating from the genome of the cell which it is desired to infect. Similarly, the promoter sequences may originate from the genome of a virus, including that of the virus used. In this connection, the E1A, MLP, CMV, RSV LTR, and the like, promoters may, for example be mentioned. In addition, these expression sequences may be modified by adding activation or regulatory sequences or sequences permitting a tissue-specific expression. It can, in effect, be especially advantageous to use expression signals which are active specifically or predominantly in vascular smooth muscle cells, so that the suicide gene is expressed and produces its effect only when the virus has actually infected a vascular smooth muscle cell. Among promoters which are active specifically or predominantly in vascular smooth muscle cells, the promoter of α-actin of smooth muscle may be mentioned in particular.

In a particular embodiment of the invention, a defective recombinant adenovirus is used which comprises a suicide gene under the control of a viral promoter, preferably chosen from the RSV LTR and the CMV early promoter.

According to another advantageous embodiment, the promoter used is one which is active specifically or predominantly in vascular smooth muscle cells.

The present invention thus provides an especially effective method for the treatment of restenosis. Moreover, to increase further the efficacy and specificity of the treatment, the Applicant has developed a method permitting a local administration of the recombinant adenoviruses at the sites to be treated. More especially, this method is based on the use of an angioplasty balloon coated with a hydrophilic film (for example a hydrogel) impregnated with adenovirus, which may thus be applied precisely to the site to be treated and permit a local and effective release of the adenoviruses at the cells to be treated.

In addition, the Applicant showed that, on healthy arteries, this method of administration made it possible to infect a high percentage of cells of the media (up to 9.6%), which are the most logical targets for the prevention of restenosis.

In a most particularly advantageous aspect, the Applicant also showed that the virus and the method of the invention permitted an effective and selective transfer of genes into an atheromatous artery. More especially, the Applicant has demonstrated for the first time the capacity of adenoviruses to transfer a therapeutically effective gene into an atheromatous artery. This is absolutely essential, since the therapeutic efficacy of the treatment of restenosis is conditional on a demonstration of the capacity to transfer the therapeutic gene, into the correct cells and with suitable efficacy, under the physiopathological conditions. Atheromatous arteries are characterized by the presence in the intima (i) of deposits of extracellular matrix, (ii) of lipid deposits consisting essentially of foam cells of the macrophage type and (iii) of proliferating smooth muscle cells.

The results presented below show that, in these atheromatous arteries, the viruses according to the invention permit a lower percentage of infection but which is of greater specificity (taking account, in fact, of the presence of macrophage type cells in this case, macrophage cells not being transduced) and which is accompanied by a substantial therapeutic efficacy. The results obtained show, in particular, a very selective transfer of the adenovirus into the target cells, that is to say the proliferating smooth muscle cells. Out of the whole cell population present in the atheromatous zone, more than 95% of the infected cells are vascular smooth muscle cells. Thus, the macrophage cells present in the intima are not infected at all (no infected macrophage cell was detected). As regards the proliferating smooth muscle cells (in the neointima), the treatment according to the invention enables a percentage of less than 1% (for example 0.2%) to be infected. This is much less than the results described previously in healthy arteries or those possessing lesions of the wall but which do not represent a physiopatholigical situation of restenosis (endothelial abrasion of a healthy artery). The Applicant also showed that the infection of this small percentage of cells nevertheless permitted a substantial therapeutic effect, demonstrated, in particular, by measurement of the luminal diameter. This result is especially surprising and implies the existence of an induced cytotoxic effect ("bystander" effect) in vivo. Hence the invention describes for the first time a method permitting the selective transfer of genes into proliferating vascular smooth muscle cells in an atheromatous artery, comprising the administration into the said artery of a defective recombinant adenovirus containing the said gene by means of an angioplasty balloon catheter. The term selective transfer implies a transfer essentially into the proliferating vascular smooth muscle cells and no transfer into the surrounding macrophage cells. This method permits a treatment of restenosis by transfer of a suicide gene such as the TK gene, followed by treatment with ganciclovir or acyclovir, for example. This method of treatment is, in addition, characterized by an effect of toxicity induced in vivo.

Another subject of the present invention relates to a pharmaceutical composition comprising a defective recombinant adenovirus and a hydrogel. More specifically, the invention relates to a composition comprising a defective recombinant adenovirus containing a suicide gene, and a hydrogel. The hydrogel used in the context of the present invention may be prepared from any biocompatible and non-cytotoxic (homo- or co-)polymer. Such polymers have, for example, been described in Application WO93/08845. Some of them, such as, in particular, those obtained from ethylene oxide and/or propylene oxide, are commercially available.

The method of treatment of the invention hence advantageously consists in introducing, at the site to be treated, a composition comprising a hydrogel impregnated with recombinant adenoviruses. The hydrogel may be deposited directly on the surface of the tissue to be treated, for example during a surgical intervention. Advantageously, the hydrogel [lacuna] be introduced into the site to be treated by means of a catheter, for example a balloon catheter, in particular during angioplasty, thereby enabling any additional trauma due to a further intervention at the angioplasty site to be avoided. It is especially advantageous for the impregnated hydrogel to be introduced into the site to be treated by means of a balloon catheter protected by a sleeve. As described in the examples, the hydrogel possesses a large number of advantages: it enables sliding of the balloon to be improved, thereby enabling it to pass through heavily stenosed arteries. Furthermore, the hydrogel can be used with any type of angioplasty balloon, which enables perfusion balloons to be used in particular. Thus, according to a particular embodiment, the adenoviruses according to the invention are administered by means of perfusion balloons, especially channelled balloon catheters ("channelled balloon angioplasty catheter", Mansfield Mecical, Boston Scientific Corp., Watertown, Mass.). The latter consists of a conventional balloon covered with a layer of 24 perforated channels which are perfused via an independent lumen through an additional infusion orifice. These perfusion balloons, which make it possible to maintain a blood flow and thus to decrease the risks of ischaemia of the myocardium, on inflation of the balloon, also enable a medicinal product to be delivered locally at normal pressure for a relatively long time, more than twenty minutes, which is necessary for an optimal infection.

It is especially advantageous to use a perfusion balloon catheter coated with hydrogel. In this case, the advantages of both, that is to say the possibility of keeping the balloon inflated for a longer period of time by retaining the properties of facilitated sliding and of site-specificity of the hydrogel, are gained simultaneously. In this case, an optimal efficacy of infection is obtained.

The results presented in the examples demonstrate, in fact, the efficacy of this system for the percutaneous transfer of genes into the arterial walls.

Another subject of the present invention relates to a pharmaceutical composition comprising a defective recombinant adenovirus and poloxamer. More specifically, the invention relates to a composition comprising a defective recombinant adenovirus containing a suicide gene, and poloxamer. Poloxamer 407 is a non-toxic, biocompatible polyol; it is commercially available (BASF, Parsippany, N.J.).

Hence a method of treatment of the invention advantageously consists in introducing, into the site to be treated, a composition comprising poloxamer impregnated with recombinant adenoviruses. The poloxamer may be deposited directly on the surface of the tissue to be treated, for example during a surgical intervention. Advantageously, the poloxamer may be introduced into the site to be treated by means of a catheter, for example a balloon catheter, in particular during angioplasty, thereby enabling any additional trauma due to a further intervention at the angioplasty site to be avoided. It is especially advantageous for the impregnated poloxamer to be introduced into the site to be treated by means of a balloon catheter protected by a sleeve. Poloxamer possesses essentially the same advantages as hydrogel while having a lower viscosity.

It is especially advantageous to use a perfusion balloon catheter coated with poloxamer, especially channelled balloon catheters. In this case, the advantages of both, that is to say the possibility of keeping the balloon inflated for a longer period of time while retaining the properties of facilitated sliding and of site-specificity of the poloxamer, are gained simultaneously. In this case also, an optimal efficacy of infection is obtained.

The present invention will be described more completely by means of the examples which follow, which are to be considered to be illustrative and non-limiting.

GENERAL TECHNIQUES OF MOLECULAR BIOLOGY

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, phenol or phenol/chloroform extraction of proteins, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., (1982); Ausubel F. M. et al. (eds), "Current Protocols in Molecular Biology", John Wiley & Sons, New York, (1987)].

Plasmids of the pBR322 and pUC type and phages of the M13 series are of commercial origin (Bethesda Research Laboratories).

To carry out ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling in of 5' protruding ends may be performed with the Klenow fragment of *E. coli* DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

In vitro site-directed mutagenesis using synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis K. B. and Faloona F. A., Meth. Enzym. 155 (1987) 335–350] technique may be performed using a "DNA thermal cycler" (Perkin Elmer Cetus) according to the manufacturer's specifications.

The verification of the nucleotide sequences may be performed by the method developed by Sanger et al. [Proc. Natl. Acad. Sci. USA, 74 (1977) 5463–5467] using the kit distributed by Amersham.

EXAMPLES

Example 1

Figure 1:
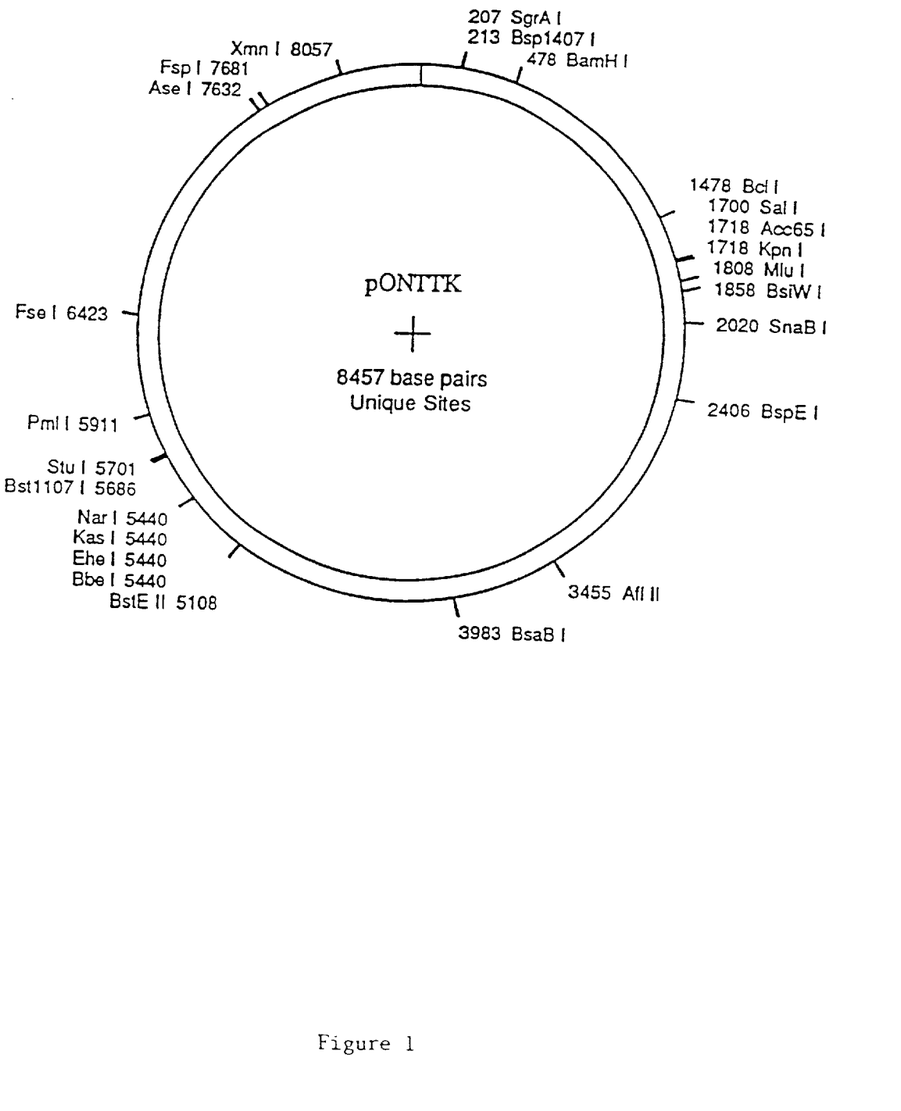
FIG. 1: Diagram of the vector pONT-tk
Figure 2:
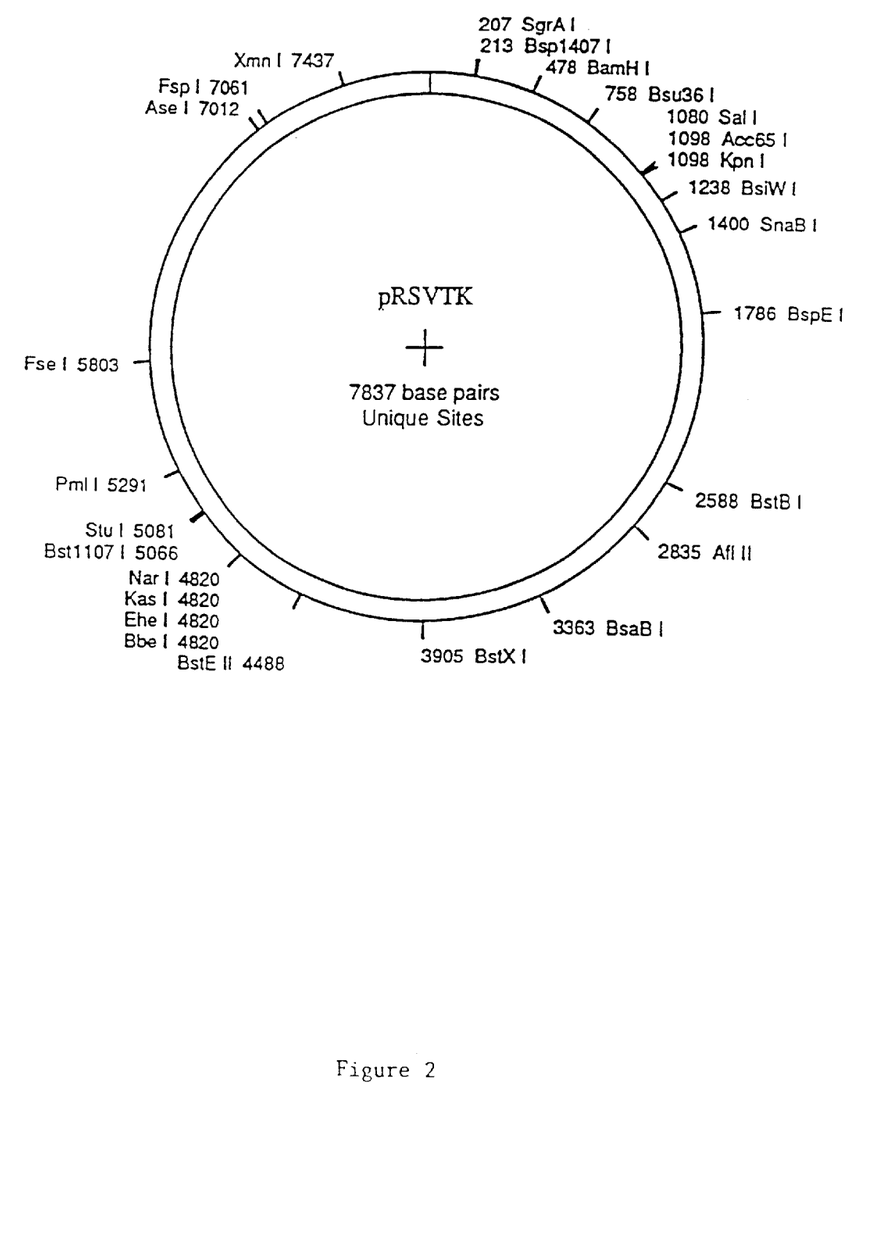
FIG. 2: Diagram of the vector pRSV-tk

Construction of the Vector Ad-LTR-TK Carrying the TK Gene under the Control of the Rous Sarcoma Virus LTR (RSV LTR) Promoter (FIG. 1)

This example describes the construction of a recombinant adenovirus comprising the herpes simplex virus thymidine kinase (tk) gene under the control of a viral promoter (RSV LTR promoter). This adenovirus was constructed by homologous recombination between the defective adenovirus Ad-dl1324 and plasmid pRSVtk carrying the tk gene under the control of the RSV promoter (Example 1.3.). This plasmid was constructed from plasmid pONTtk (Example 1.1.) by substituting the RSV promoter for the promoter which can be transactivated by EBNA1 (Example 1.2.).

1.1. Construction of Plasmid pONTtk a) Construction of Plasmid p7tk1

This example describes the construction of plasmid p7tk1 containing the 1131-base pair open is reading frame of the tk gene (ATG 114–116 and stop codon TGA 1242–1244), inserted into a multicloning site.

The BglII-NcoI fragment containing the herpes simplex type 1 virus thymidine kinase (tk) gene was isolated from plasmid pHSV-106 (marketed by Gibco BRL), repaired by the action of the Klenow fragment and then inserted at the SmaI site of plasmid pGEM7zf(+) (marketed by Promega). The SmaI and BglII sites are destroyed during this step, the NcoI site is preserved.

The Plasmid Obtained was Designated p7tk1 b) Construction of Plasmid pONT1

This example describes the construction of a plasmid containing a chimeric promoter consisting of a sequence needed for transactivation by the antigen EBNA1 and of the EBV virus TP1 promoter.

The EcoRI(7315)-SmaI(8191) fragment of the EBV virus was isolated from the strain B95-8. The complete sequence of the EBV virus has been described by Baer et al. (Nature 310 (1984) 207). This fragment contains the sequences needed for transactivation by the nuclear antigen 1 (EBNA1) (D. Reisman & B. Sugden, 1986, Molecular and Cellular Biology, vol. 6 pp. 3838–3846). This fragment was then fused to the NruI(166 241)-PstI(166 559) fragment of EBV B95-8 (the PstI site was digested with T4 polymerase), containing the TP1 promoter. The chimeric promoter thereby obtained was then inserted into the multicloning site of the plasmid pBluescript II SK to generate plasmid pONT1.

c) Construction of Plasmid pONTtk

Plasmid pONTtk contains the herpes simplex virus thymidine kinase (tk) gene cloned into plasmid p7tk1, under the control of the chimeric promoter EBNA1-RE/TP1cloned into plasmid pONT1.

To construct this plasmid, the BamHI-XhoI fragment of pONT1, which contains the chimeric promoter transactivated by EBNA-1 and EBNA-2, and the XhoI-ClaI fragment of p7tk1, which contains the open reading frame of tk, were cloned at the BamHI (478) and ClaI (4550) sites of plasmid pAd.RSVbgal. Plasmid pAd.RSVbGal contains, in the 5'→3' orientation, the PvuII fragment corresponding to the left-hand end of the Ad5 adenovirus comprising: the ITR sequence, the origin of replication, the encapsidation signals and the E1A enhancer;

the gene coding for b-galactosidase under the control of the RSV (Rous sarcoma virus) promoter, a second fragment of the Ad5 adenovirus genome, which permits homologous recombination between plasmid pAd.RSVbGal and the adenovirus dl324. Plasmid pAd.RSVbGal has been described by Stratford-Perricaudet et al., (J. Clin. Invest. 90 (1992) 626).

All the cloning sites are preserved. The plasmid obtained was designated poNTtk.

1.2. Construction of Plasmid pRSVtk

This plasmid was constructed from plasmid pONTtk (Example 1.1.) by substituting the RSV promoter for the promoter which can be transactivated by EBNA1. To this end, the RSV promoter was isolated in the form of a BamHI-SalI fragment from plasmid pAd.RSV.βgal (Stratford-Perricaudet et al., J. Clin. Invest. 90 (1992) 626), and then cloned at the BamHI(478) and SalI(1700) sites of plasmid pONTtk. The resulting plasmid was designated pRSVtk (FIG. 1).

1.3. Construction of the Recombinant Adenovirus Ad-RSV-tk

The vector pRSVtk was linearized and cotransfected with a defective adenoviral vector into helper cells (line 293), providing in trans the functions-encoded by the adenovirus E1 (E1A and E11B) regions.

More precisely, the adenovirus Ad-RSV-tk was obtained by in vivo homologous recombination between the mutant adenovirus Ad-dl1324 (Thimmappaya et al., Cell 31 (1982) 543) and the vector pRSVtk, according to the following protocol: plasmid pRSVtk, linearized with XmnI, and the adenovirus Ad-dl1324, linearized with the enzyme ClaI, were cotransfected into line 293 in the presence of calcium phosphate, to permit homologous recombination. The recombinant adenoviruses thus generated were selected by plaque purification. After isolation, the recombinant adenovirus DNA was amplified in cell line 293, leading to a culture supernatant containing the unpurified defective recombinant adenovirus having a titre of approximately $10^{10}$ pfu/ml.

The viral particles were then purified by centrifugation on a caesium chloride gradient according to known techniques (see, in particular, Graham et al., Virology 52 (1973) 456). The adenovirus Ad-RSV-tk may be stored at −80° C. in 20% glycerol.

Example 2

Activity of an Adenovirus According to the Invention in the Presence of Ganciclovir on Smooth Muscle Cells in Culture The activity of the adenovirus containing the TK gene, prepared in Example 1, was checked on in vitro models of smooth muscle cells. To this end, smooth muscle cells isolated from rat and rabbit aorta were infected with the recombinant adenovirus Ad-RSV-tk and incubated in the presence of ganciclovir. The effect of the Ad-RSV-tk/ganciclovir combination on cell viability is then confirmed by the colorimetric test employing MTT, 3-(4,5-dimethylthiazol-2-yl)-2,5-diphenyl-tetrazolium bromide, according to the technique described by Mosman (J. Immunol. Meth. 65 (1983) 55), or more accurately by cell counting. Briefly, vascular smooth muscle cells (VSMC) are set up in culture by enzymatic digestion of NZW rabbit aorta according to a method adapted from Chamley et al. (Cell Tissue Res. 177: 503–522 1977). The cells are maintained in the presence of 20% of foetal calf serum and used for all the tests (see below) before the tenth passage. In all our experiments, smooth muscle cells are characterized by immunolabelling using anti-αSM-actin antibody (Sigma).

In order to measure the cytotoxic activity of the Ad-RSV-TK/ganciclovir combination, rabbit aorta VSMC are incubated in the presence of the adenovirus diluted in culture medium (DMEM, 0.5% FCS). After approximately one hour at 37° C. in a humid atmosphere, the medium containing the adenoviral solution is aspirated off and replaced by culture medium (DMEM, 0.5% FCS) for a period of 18 to 24 hours. Different concentrations of ganciclovir are then added in an FCS-rich (10%) medium. Four days after the addition of ganciclovir, the cells are counted (100% cell viability corresponding to cells not transduced with Ad-RSV-TK and not treated with ganciclovir).

Figure 3:
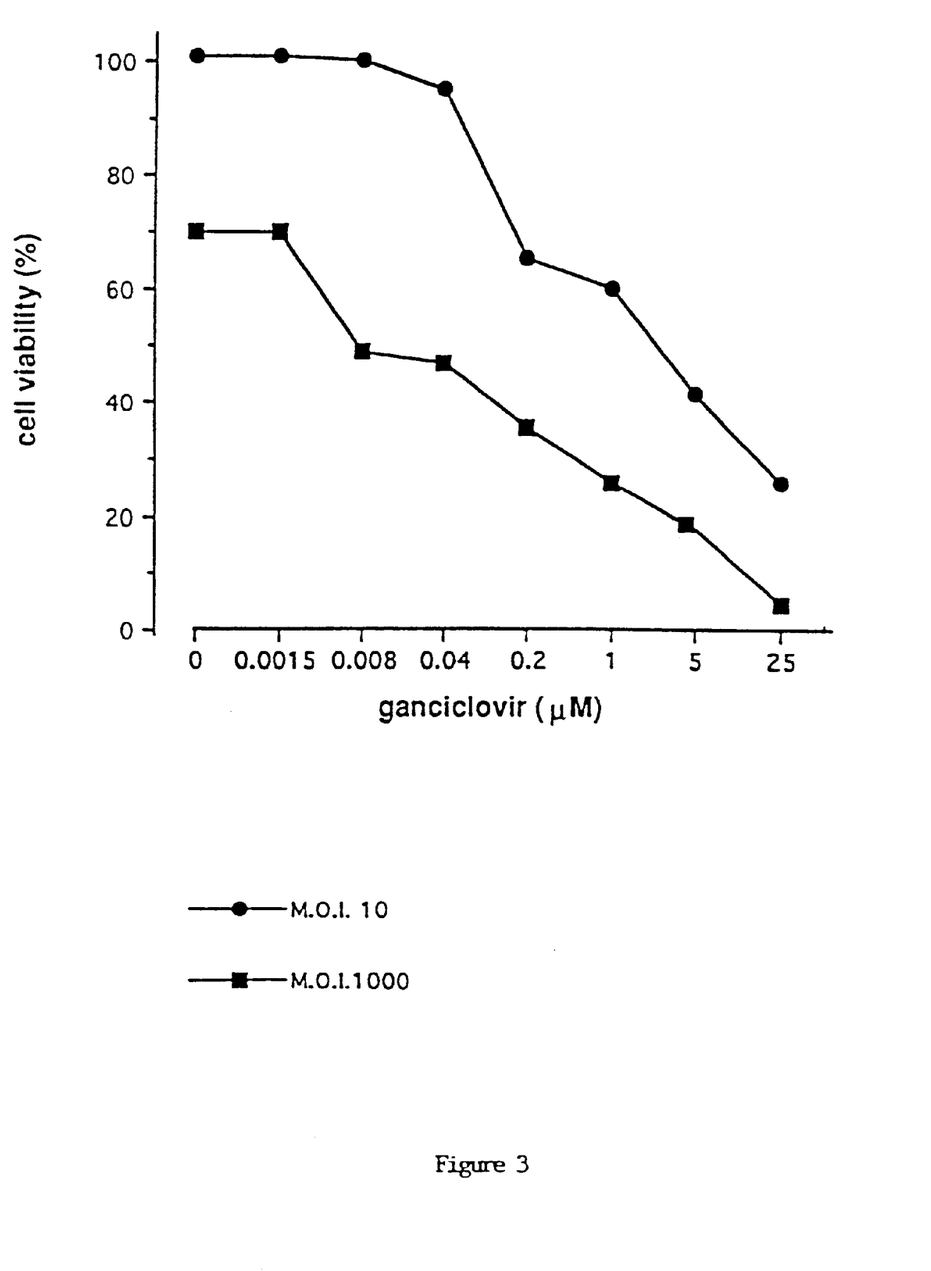
FIG. 3: Cytotoxic effect of the ganciclovir/Ad-LTR-tk combination on smooth muscle cells in culture.
Figure 4:
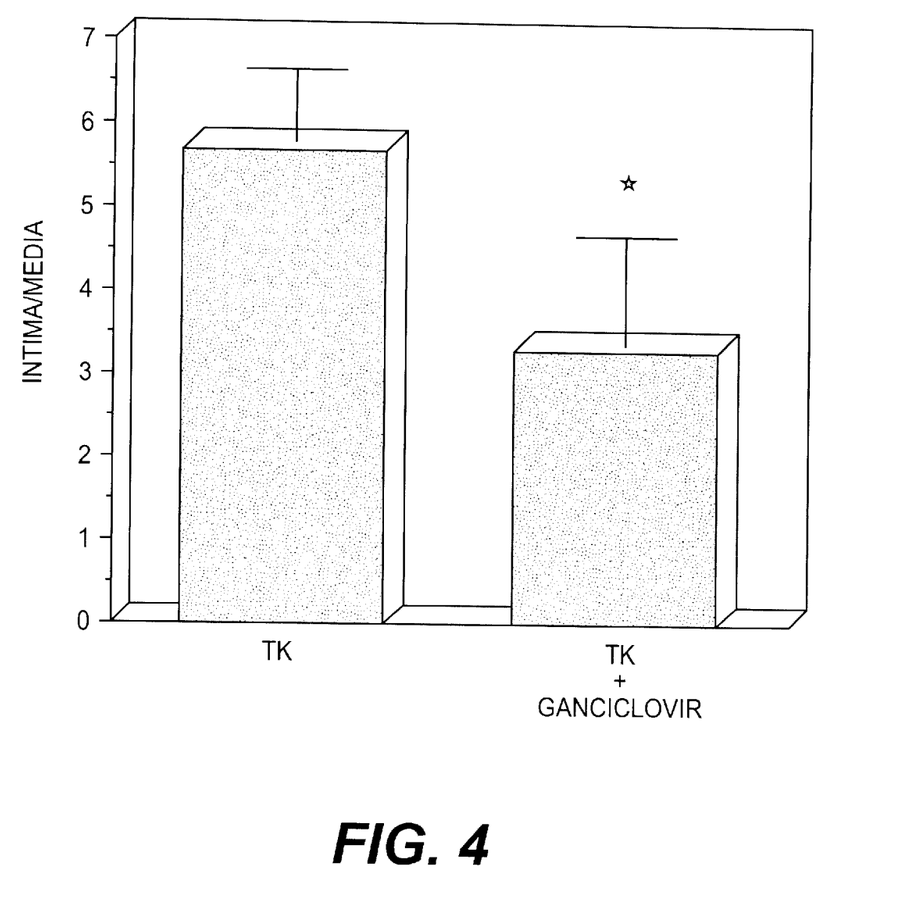
FIG. 4: Reduction of restenosis by adenoviral transfer of the tk gene and administration of ganciclovir.

The Ad-RSV-TK/ganciclovir combination induces a cytotoxic effect with respect to rabbit VSMC (see FIG. 3). This cytotoxicity varies in accordance with the ganciclovir concentration and the multiplicity of Ad-RSV-TK infection. Under our experimental conditions, i.e. four days of incubation in the presence of 10% FCS, the Ad-RSV-TK (M.O.I. 1000)/ganciclovir (25 μM) combination brings about complete cytolysis. Under these experimental conditions where a high multiplicity of infection enables the majority of the cells to be transduced, the $IC_{50}$ is 0.3 μM. At a low multiplicity of infection (M.O.I. 10), the $IC_{50}$ is less than 5 μM. Thus, the concentrations of ganciclovir which are active in vitro on SMC are compatible with a therapeutic use. In effect, in patients treated for viral infection with a non-toxic dose of ganciclovir, it is possible to reach plasma concentrations above 15 μM (Paul and Dummer, Am. J. Med. Sci. 4: 272–277, 1992).

In addition, this in vitro study demonstrates that it is possible to induce a major cytotoxic effect in spite of a small percentage of transduction by the Ad-RSV-TK adenovirus. The presence of the HSV-TK protein was demonstrated by indirect immunofluorescence using monoclonal antibodies specific for HSV-TK (monoclonal antibody 4C8, Yale University). In rabbit (and human) VSMC treated with Ad-RSV-TK, the localization of the TK protein is cytoplasmic but also nuclear. We have shown in this way that the use of a multiplicity of infection of 10 is associated with a transduction of fewer than 5% of the VSMC. Generally speaking, at an equivalent multiplicity of infection, the percentage of cells transduced by Ad-RSV-TK is similar to that obtained using a control adenovirus coding for β-galactosidase (e.g. more than 90% of cells transduced at a multiplicity of infection of 1000). These data hence demonstrate that the transduction of fewer than 5% of VSMC brings about a substantial cytotoxicity in the presence of an optimal concentration of ganciclovir (see FIG. 3: 80% drop in cell viability at 25 μM). Immunodetection of the HSV-TK protein hence illustrates the magnitude of the "bystander"

effect observed on VSMC treated with the Ad-RSV-TK/ganciclovir combination. This "bystander" effect may have its counterpart in vivo. In particular, these data strongly suggest that a limited transfer of Ad-RSV-TK adenovirus, in particular into a pathological artery, may lead to a significant reduction of the neointimal mass, which is rich in SMC and responsible for restenosis in the patient.

Moreover, the cytolytic effect is selective, since neither simple treatment with ganciclovir nor transduction with Ad-RSV-TK per se is associated with cell death. The cytotoxicity of the Ad-RSV-TK/ganciclovir combination has been confirmed by the calorimetric test employing MTT. Lastly, similar results, namely a selective toxicity in the presence of ganciclovir and adenovirus, have been observed on a primary culture of human smooth muscle cells.

Hence these data demonstrate the effective blocking of the proliferation of VSMC in vitro by Ad-RSV-TK.

Example 3

Arterial Transfer of a Recombinant Adenovirus Via the Percutaneous Route

This example describes the development of an especially effective technique for gene transfer via the percutaneous route. This technique is based on the use of a balloon catheter with hydrogel. The results presented show that, most advantageously, this technique enables certain favoured cell populations to be infected effectively, in particular for the treatment of restenosis.

This example was carried out using a defective recombinant adenovirus comprising the *E. coli* β-galactosidase gene under the control of the RSV RSV promoter and of a nuclear localization signal. The construction of this adenovirus has been described, in particular, in Stratford-Perricaudet et al., (J. Clin. Invest. 90 (1992) 626).

The experiments were carried out on New Zealand white rabbits anaesthetized with acepromazine and maintained under pentobarbital. Gene transfer was performed at the external iliac artery.

The adenovirus Ad-RSV.β-Gal ($1-2 \times 10^{10}$ pfu in 100 µl of phosphate buffer) was deposited on a balloon catheter previously coated with hydrogel (Hydroplus, Mansfield Medical, Boston Scientific Corp., Watertown, Mass.) (Riessen et al., Hum. Gene Ther. 4 (1993) 749). The catheter used is a balloon catheter 2 cm in length and between 2.5 and 3 mm in diameter. The catheter was then introduced, using a protective sleeve, into the right femoral artery. A pressure of one atmosphere was then applied, and the catheter was thereafter directed into the external iliac artery where a pressure of 6 atmospheres was then applied to the balloon for 30 minutes. This experiment was carried out on 27 rabbits. 3 to 28 days after administration, the animals were sacrificed by overdosing with pentobarbital.

Transfer of the Gene into the Arterial Wall and its Expression Therein

The arteries of the sacrificed animals were isolated, and the expression of β-galactosidase was detected by staining in the presence of X-gal according to the technique of Sanes et al., (EMBO J. 5 (1986) 3133). For each animal, at least two arterial segments were either mounted on OCT (Miles Laboratories Inc.; IL) for frozen-section experiments, or coated with paraffin, cut into 6 µm sections and counterstained with haematoxylin and eosin. Expression was considered positive only when a deep blue colouration was observed in the nucleus. The results obtained show clearly that the arteries of the infected animals display a blue colouration characteristic of β-gal. A microscopic analysis discloses that there is no residual intact endothelium, but that the continuity of the internal elastic lamina is preserved. Microscopic analysis also shows that the cells of the media have been infected with the adenoviruses and express the transferred gene. More precisely, whereas, in the case of an administration by double-balloon catheter, only 0.4% of the cells of the media have been infected, 9.6% are infected using a balloon catheter coated with hydrogel (see morphometric analysis below). Furthermore, the 9.6% are calculated relative to the total thickness of the media but, in the superficial layers of the media, 100% of the cells are infected. These results are far better than those obtained with double-balloon catheters, or by transfer of naked genes or by means of liposomes. These experiments demonstrate the extent to which adenoviruses can constitute an especially advantageous vector for the administration of suicide genes for the purpose of treatment of restenosis.

Morphometric Analysis

The efficacy of transfer was determined on 7 treated rabbits. All these animals received $5 \times 10^9$ pfu of adenovirus to infect an arterial segment 2 cm in length, so that the multiplicity of infection is similar for each animal. For each iliac artery transfected, two serial segments 5 mm in length were taken from the target zone and, for each segment, at least three sections at random were examined under the light microscope after staining with X-gal. On each section, the efficacy of transfer was determined from the ratio of stained media cells to the total number of media cells. In all, more than $30 \times 10^3$ cells originating from arteries infected with the adenoviruses (48 sections) were counted. The mean percentage of infected media cells is 4.02%, with values which can reach 9.6%. In the case of a transfer with a double-balloon cathether, the mean percentage is only 0.18%.

Kinetics of Expression

To determine the duration of expression of the gene transferred by the adenoviruses according to the invention, a study of the expression of β-gal was carried out over time on 20 rabbits treated either using a double-balloon catheter (10 animals) or using a balloon catheter impregnated with hydrogel (10 animals). For each group, 2 animals were sacrificed on days 3, 7, 14, 21 and 28. Expression was detected by macroscopic and microscopic examination of arteries stained with X-gal as described above. The results obtained show, for each group, a stable expression for 14 days, followed by a drop at 21 days. No expression is detected at 28 days. The same kinetics could be demonstrated in a pathological artery in the atheromatous rabbit model. These results confirm the transient effect of the vectors of the invention, which is especially advantageous and suited to the treatment of restenosis, in particular on the atheromatous walls.

Selectivity of the Transfer and Expression with Respect to Arterial Walls

In order to check the possible dissemination to other tissues of the adenoviruses injected, in all the animals sacrificed 3 days after injection, tissue samples originating from the liver, brain, testicles, heart, lung, kidney and skeletal muscle, as well as an arterial segment adjacent to the site treated, were removed immediately after sacrifice. On each sample, gene transfer and expression were demonstrated by PCR (by means of probes directed against the gene coding for adenovirus protein IX and against the lacz gene) and histochemistry. The results obtained show that none of the samples removed from the animals treated with a balloon catheter coated with hydrogel displays staining in the tissues tested. Similarly, no presence of virus could be detected by PCR in the samples tested, even using an optimized and very sensitive protocol of 45 amplification cycles.

These results demonstrate the efficacy of the mode of administration according to the invention for delivering therapeutic genes very locally.

Example 4

Arterial Transfer of the Adenovirus Ad-RSV-TK

This example demonstrates the properties of the TK adenovirus of the invention for the treatment of restenosis by selective transfer into an atheromatous artery.

Animal Model

The efficacy of the arterial transfer was evaluated in a model of restenosis in New Zealand white rabbits. The rabbits were subjected beforehand to a cholesterol-rich (1%) diet for two weeks. The iliac artery was abraded by five successive inflations using a latex balloon (4F). The animals were subjected again to a hypercholesterolaemia-inducing diet for six weeks. Arterial transfer was performed percutaneously according to the procedure described above, at the damaged artery. The adenovirus Ad-RSV-TK ($4 \times 10^9$ pfu in 40 μl of phosphate buffer) was accordingly deposited on a balloon catheter previously coated with hydrogel (Hydroplus, Mansfield Medical, Boston Scientific Corp., Watertown, Mass.) (Riessen et al., Hum. Gene Ther. 4 (1993) 749). The catheter used is a balloon catheter 2 cm in length and 2.5 mm in diameter.

Based on a double lesion following abrasion and angioplasty, this model of restenosis, and not only of stenosis, enables the efficacy of adenoviral transfer of a suicide gene into an atheromatous artery to be evaluated.

In the light of the in vitro experimental data, and in order to verify the selectivity of the treatment with Ad-RSV-TK, the animals were divided into two groups, treated or otherwise with ganciclovir. The treatment with ganciclovir was prolonged for five days (from the second to the seventh day following angioplasty) at the rate of 2×25 mg/kg/day.

Morphometric Analysis

Six weeks after angioplasty, the animals were sacrificed with pentabarbital, and the iliac arteries were fixed and removed for the purpose of morphometric analysis. The contours of the lumen as well as those of the internal/external elastic limiting membranes were evaluated after staining with orcein/haematoxylin. In all, six blocks were analysed per artery, including 4 lying within the angioplasty zone and two immediately upstream and downstream of this zone. For each block, three adjacent sections were analysed. Briefly, different parameters such as luminal diameter and intima/media ratio were calculated. Samples for which these contours could not be revealed as a result of a rupture of the internal elastic limiting membrane or of a thrombotic occlusion were excluded.

Morphometric analysis reveals a high intima/media ratio in the control group which has been subjected to adenoviral transfer by angioplasty but not treated with ganciclovir (5.73+/−0.81, n=3). The severity of the lesion hence enables the efficacy of a gene transfer treatment to be evaluated on a pathological artery. In addition, as shown by the immunohistochemical study, the lesions induced in this animal model are rich in macrophages, but also rich in smooth muscle cells which constitute the therapeutic target of the gene transfer. These data collectively bring out the value of the model used, which is not based on a simple endothelial abrasion in a healthy artery, and consequently mimics at least partially the pathology of postangioplasty restenosis in man.

Morphometric analysis shows that the intima/media ratio is reduced by 42% ($p<0.05$) in the group of animals subjected to the Ad-RSV-TK/ganciclovir combination (3.30+/−1.26, n=6). The significant reduction in this parameter demonstrates that local transfer of the TK gene by a recombinant adenovirus, in combination with the administration of ganciclovir, constitutes a promising therapeutic approach as a preventive treatment for postangioplasty restenosis.

We claim:

1. A method for inhibiting proliferation of vascular smooth muscle cells comprising local administration to a site of physical damage to an atheromatous blood vessel of a replication defective recombinant adenovirus comprising:

a suicide gene operably linked to a promoter controlling expression of said gene in infected cells, a left and a right ITR, and an encapsidation signal wherein said replication defective adenovirus is of human or canine origin and wherein said inhibition of proliferation inhibits a decrease in luminal diameter of said blood vessel occurring after said physical damage to said blood vessel.

2. The method according to claim 1, wherein said suicide gene is transferred into the smooth muscle cells of an atheromatous plaque.

3. The method according to claim 1, wherein the suicide gene is selected from the group consisting of a thymidine kinase gene and a cytosine deaminase gene.

4. The method according to claim 3, wherein the suicide gene is a human herpesvirus thymidine kinase gene.

5. The method according to claim 1, wherein the promoter is a viral promoter.

6. The method according to claim 5, wherein the promoter is selected from the group consisting of a RSV LTR and a CMV promoter.

7. The method according to claim 1, wherein an E1 region and at least one region selected from the group consisting of E2, E4, and L1–L5 of said adenovirus are non-functional.

8. The method according to claim 7, wherein the E1 and E4 regions are non-functional.

9. The method according to claim 8, wherein all or part of the E1 and E4 regions are deleted.

10. The method according to claim 1, wherein the adenovirus is of the serotype Ad2 or Ad5.

11. The method according to claim 1, wherein the adenovirus is impregnated in a hydrogel.

12. The method according to claim 11, wherein the hydrogel is deposited on a balloon catheter.

13. The method according to claim 1, wherein the adenovirus is administered using a perfusion balloon catheter.

14. The method according to claim 13, wherein the catheter is a channelled balloon catheter.

15. The method according to claim 13, wherein the adenovirus is impregnated in a hydrogel.

16. The method according to claim 1, wherein the adenovirus is impregnated in poloxamer.

17. The method according to claim 13, wherein the adenovirus is impregnated in poloxamer.

18. The method according to claim 4, wherein the suicide gene is a human HSV-1 TK gene.

19. The method according to claim 1, wherein the replication defection adenovirus is administered using a device comprising a balloon catheter coated with a hydrogel, wherein said hydrogel is impregnated with the replication defective recombinant adenovirus in an amount effective for inhibiting a decrease in luminal diameter of said blood vessel occurring after physical damage to said blood vessel.

20. The method according to claim 19, wherein said gene is transferred into smooth muscle cells of the atheromatous plaque.

21. The method according to claim 20, wherein smooth muscle cells represent greater than 95% of cells into which said gene is transferred.

22. The method according to claim 21, wherein said gene encodes a thymidine kinase and said administration is followed by treatment with ganciclovir.

23. The method according to claim 22, wherein said administration induces a bystander effect.

24. The method according to claim 23, wherein greater than or equal to 0.2% of smooth muscle cells of the neointima are infected by said adenovirus.

* * * * *